United States Patent
Bärwinkel et al.

(10) Patent No.: US 9,066,737 B2
(45) Date of Patent: Jun. 30, 2015

(54) METHOD FOR MOVING AN INSTRUMENT ARM OF A LAPAROSCOPY ROBOT INTO A PREDETERMINABLE RELATIVE POSITION WITH RESPECT TO A TROCAR

(75) Inventors: Ronny Bärwinkel, Dormitz (DE);
Oliver Hornung, Fürth (DE);
Karl-Heinz Maier, Altdorf b. Nürnberg (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 127 days.

(21) Appl. No.: 13/698,076

(22) PCT Filed: Apr. 21, 2011

(86) PCT No.: PCT/EP2011/056438
§ 371 (c)(1),
(2), (4) Date: Nov. 15, 2012

(87) PCT Pub. No.: WO2011/147651
PCT Pub. Date: Dec. 1, 2011

(65) Prior Publication Data
US 2013/0066335 A1 Mar. 14, 2013

(30) Foreign Application Priority Data
May 25, 2010 (DE) .......................... 10 2010 029 275

(51) Int. Cl.
*G06F 19/00* (2011.01)
*A61B 19/00* (2006.01)

(52) U.S. Cl.
CPC .......... *A61B 19/201* (2013.01); *A61B 19/2203* (2013.01); *A61B 2019/2211* (2013.01); *A61B 2019/5214* (2013.01); *A61B 2019/5255* (2013.01)

(58) Field of Classification Search
USPC .................................. 606/130; 700/245–164
See application file for complete search history.

(56) References Cited

U.S. PATENT DOCUMENTS

| 5,417,210 A * | 5/1995 | Funda et al. ................. 600/425 |
| 6,694,164 B2 | 2/2004 | Glossop |

(Continued)

FOREIGN PATENT DOCUMENTS

| DE | 102004052753 A1 | 5/2006 |
| DE | 102008016146 A1 | 10/2009 |

(Continued)

OTHER PUBLICATIONS

L.E. Weiss and C.P. Neuman, "Dynamic Sensor-Based Control of Robots with Visual Feedback", In: IEEE Journal of Robotics and Automation, vol. RA-3, No. 4, Oct. 1987, pp. 404-417; Others; 1987.

(Continued)

*Primary Examiner* — Bhavesh V Amin

(57) ABSTRACT

A method for moving an instrument arm of a laparoscopy robot into a predeterminable position relative to a trocar placed in a patient is proposed. A spatial marker that can be localized from outside of the patient is applied to the trocar. The spatial position of the trocar is detected based on the spatial marker. The intended position of the instrument arm is established from the spatial position and the relative position. The actual position of the instrument arm is detected. The instrument arm is moved into the intended position based on the actual position, the intended position and an error minimization method.

7 Claims, 2 Drawing Sheets

(56) References Cited

U.S. PATENT DOCUMENTS

| | | | |
|---|---|---|---|
| 7,347,862 B2* | 3/2008 | Layer | 606/130 |
| 2003/0114731 A1* | 6/2003 | Cadeddu et al. | 600/114 |
| 2003/0120283 A1* | 6/2003 | Stoianovici et al. | 606/130 |
| 2005/0148854 A1* | 7/2005 | Ito et al. | 600/407 |
| 2006/0258938 A1 | 11/2006 | Hoffman | |
| 2007/0078334 A1* | 4/2007 | Scully et al. | 600/424 |
| 2007/0173977 A1* | 7/2007 | Schena | 700/263 |
| 2008/0082108 A1 | 4/2008 | David | |
| 2009/0088897 A1 | 4/2009 | Hasser | |
| 2010/0081875 A1 | 4/2010 | Allen | |
| 2013/0331644 A1* | 12/2013 | Pandya et al. | 600/102 |

FOREIGN PATENT DOCUMENTS

| | | |
|---|---|---|
| DE | 102008041260 A1 | 2/2010 |
| EP | 1854425 A1 | 11/2007 |
| WO | WO 0146577 A2 | 6/2001 |

OTHER PUBLICATIONS

J. Wang and W.J. Wilson, "3D relative position and orientation estimation using Kalman filter for robot control", IEEE Int. Conf. on Robotics and Automation, pp. 2638-2645 (1992), URL: http://ieeexplore.ieee.org/stamp/stamp.jsp?tp=&arnumber=220044; Others; 1992.

daVinci Prostatectomy—Changing the Experience of Prostate Surgery, Intuitive Surgical, Inc., PN 871010 Rev. A7/2005; Others; 2005; US.

Alexandre Krupa et al., "Autonomous 3-D Positioning of Surgical Instruments in Robotized Laparoscopic Surgery Using Visual Servoing", IEEE Transactions on Robotics and Automation, IEEE Inc. New York, US, vol. 19. No. 5, Oct. 1, 2003, pp. 842-853; Others; 2003.

\* cited by examiner

METHOD FOR MOVING AN INSTRUMENT ARM OF A LAPAROSCOPY ROBOT INTO A PREDETERMINABLE RELATIVE POSITION WITH RESPECT TO A TROCAR

CROSS REFERENCE TO RELATED APPLICATIONS

This application is the US National Stage of International Application No. PCT/EP2011/056438 filed Apr. 21, 2011 and claims the benefit thereof. The International Application claims the benefits of German application No. 10 2010 029 275.3 filed May 25, 2010, both of the applications are incorporated by reference herein in their entirety.

FIELD OF THE INVENTION

The invention relates to a method for moving an instrument arm of a laparoscopy robot into a predeterminable relative position with respect to a trocar that has been introduced into a patient.

BACKGROUND OF THE INVENTION

Minimally invasive interventions are acquiring an increasing significance in the field of clinical surgery. Although, only a few years ago, relatively large areas of the operating site were opened up for small surgical interventions in order to allow the surgeon to navigate using natural landmarks, it can be observed that nowadays a large number of these interventions are carried out using laparoscopy and optical assistance in the form of endoscopy. Robot-assisted surgery is a further development of traditional laparoscopy that has made inroads meanwhile in a number of areas of medicine, for example, in urology, gynecology or cardiology. It is in the process of becoming part of the everyday medical scene.

A laparoscopy robot is known, for example, in the form of the "da Vinci" model from the company Intuitive Surgical. This robot comprises a first instrument arm that has an endoscope at its front extremity. Up to three further instrument arms hold laparoscopic instruments.

Both for the endoscope and for each of the instruments, a trocar is placed in the patient in each case. The trocar is used to introduce the respective tool into the patient in order to then carry out a robot-assisted, minimally invasive intervention on the patient.

It may be observed in the clinical workflow of such an intervention that a considerable proportion of the surgical preparation time consists in inserting the tools controlled by the robot on the instrument arms into the trocars that have already been set up in the run-up to the surgery or in preparing for the insertion of these tools. For this purpose, the individual articulations, linear actuators and so forth on the respective robotic arm are connected without power and the instrument arm is adjusted by hand in such a way that, through the corresponding adjustments of the articulations or of the underlying kinematics for the robot, the instrument (which is still outside the patient), comes to rest in a predetermined relative position, which may also be understood as a target position, with respect to the trocar. Here the trocar is already placed in an individual spatial location in the patient (which location is more or less spatially fixed) with a trocar providing a trocar axis, generally the central longitudinal axis, as the direction in which the longitudinal tools are introduced axially into the patient via the trocar.

In the da Vinci System, the instrument arm can be oriented together with the instrument (usually in three dimensions) such that the longitudinal axis of the instrument that is being held runs coaxially to the trocar axis, but the instrument remains, however, at a distance from the trocar and is located outside the patient. In other words, the predetermined relative position is such that the instrument on the instrument arm can impact on or penetrate the trocar with a movement in a straight line. The instrument can then still be moved unidimensionally in this axial direction towards the trocar until it touches it. The instrument arm is then again mechanically coupled; the instruments are then introduced robotically into the respective trocar with a movement in a straight line. In other words, there is therefore a predeterminable relative position for the instrument arm that can be targeted, which position is predeterminable with respect to a trocar placed in a patient.

This procedure of manual adjustment assumes that the staff carrying out the reparation has some experience and it is very time-consuming. Even in mechanically complex systems, the manual adjustment is very elaborate since, for safety reasons, a very high friction level has to be selected in the articulations even when in power-free operation. In the case of the aforementioned da Vinci System, this procedure has to be repeated four times when all the robot arms are used.

SUMMARY OF THE INVENTION

The object of the present invention is to provide an improved method for moving an instrument arm of a laparoscopy robot into a predeterminable relative position with respect to a trocar that has been introduced into a patient.

The object is achieved by a method according to the claims. According to the invention, a spatial marker that is locatable from outside the patient is fitted to the trocar. The spatial position of the trocar is determined using the spatial marker. For example, the spatial position, that is, the position and orientation of the trocar in, for example, a system of coordinates that is in a spatially fixed position in the operating theater, is therefore detected by a navigation system with the aid of the spatial marker. From the spatial position and the predetermined relative position of the instrument arm with respect to the trocar, the desired position of the instrument arm in the theater is then determined.

In a subsequent step, the actual position of the instrument arm in the theater is determined. For this purpose, it is possible, for example, for a locatable spatial marker also to be fitted on the instrument arm, so that the spatial position can thus be determined as the actual position of the instrument arm. However, the spatial position can also be determined using position recorders in the robotic arm at a known position of a base support pertaining to the robot or using other methods.

Using the actual position and the desired position of the instrument arm, the instrument arm is then moved into the desired position with the aid of an error minimization method. In other words, the constant actual position of the instrument arm is followed up continually, that is during movement, and it is achieved by means of the error minimization method that the actual position increasingly approximates the desired position and is finally integrated therein. In the desired position, the instrument arm is then in the predeterminable relative position with respect to the trocar.

Locating is based, for example, on at least three markers that are arranged statically on the trocar on the outside of the patient's body or connected thereto. Camera images from the markers are then logged and tracked, by, for example, a CCTV-camera. An advantageous feature is the selection of markers that can be segmented very easily in the camera image. For example, infrared (IR)-reflecting markers and an IR light source from the direction of the camera can be used. Such an apparatus is known, for example, from tracking devices such as the "Polaris" system available from the NDI company.

The method according to the invention is suitable both for an individual instrument arm of a multi-arm robot and for the aforementioned single-arm, single-port robot. The gain in valuable operating time, the shorter anesthesia time and simpler operation of the device are the direct consequences of the method according to the invention.

Furthermore, the movement of the robotic arm according to the method may be achieved manually. For example, as a result of the error minimization according to the method, however, adjustment movements that are to be carried out for individual articulations or degrees of freedom of the robot are suggested to the operator. Thus the manual movement of the instrument arm can be targeted or result-oriented and therefore carried out in a clearly improved manner or accelerated. This means that the operating team in charge no longer has to "feel their way" and adjust the robotic arm "by instinct", but receives specific assistance thanks to the method according to the invention as a result of specifically directed adjustment suggestions.

In an advantageous embodiment of the method, however, the instrument arm is automatically moved into the desired position. This consequently results in a fully automated orientation of the instrument arm with respect to the trocar, that is, completed mechanically by the robot itself. Subsequently, it is then possible to start immediately on the actual treatment of the patient or with the first step thereof, that is, the robot-assisted insertion of the instruments into the patient.

The relative position may still allow a degree of freedom: if, for example, the relative position is set in such a way that the instrument is coaxial to the axis of the through passage of the trocar, the remaining manual surgical preparation required by the team is reduced from a three-dimensional to a one-dimensional problem: the instrument now only has to be pushed forward axially up to the trocar along one line, that is, for example, along the central longitudinal axis of the trocar, in order to finally align the robot with the patient. This manual step is, for example, that of placing the instrument in contact with the trocar and thus defining a zero position in the system.

In a preferred embodiment of the method, the relative position is selected such that it guarantees a coaxial alignment of an instrument that is introducible axially into the trocar and that is fitted on the instrument arm. More specifically, there ensues a coaxial alignment of an instrument axis forming, for example, a central longitudinal axis of an instrument with a trocar axis forming, for example, the central longitudinal axis of the trocar. The position of the instrument is therefore defined as a relative position or target position. This is particularly suitable for robots in which the instrument itself is adjustable in an axial direction—for example, to manually achieve a touching zero position on the trocar. The aforementioned position outside the patient and at a safe distance from the trocar can then be selected as a relative position.

In a further advantageous embodiment, the spatial position of the trocar and/or the actual and desired position of the instrument arm are determined by optical detection using a camera. In other words, an optically functioning navigation system is then used for the locating process. The optical detection occurs, for example, using a camera, and the spatial markers are then optically visible. Possible options for markers are, for example, at least three marker points fitted on the trocar, which points can be detected by the camera. Known camera systems operate using visible light or infra-red light.

In a preferred embodiment of the method, the aforementioned optical detection of the corresponding positions or markers is achieved in such a way that, for this purpose, an endoscope arranged on one of the instrument arms of a robot is used as a camera. In other words, according to said configuration, the endoscope, which has camera functionality anyway, is also used outside the patient as a navigation camera. If, moreover, the endoscope is arranged on that instrument arm that is intended to be moved into the relative position, an additional step in the position determination of the instrument arm becomes superfluous: the camera itself then contains in its system the instrument arm position that is to be tracked. In other words, the respective actual position or desired position devolves into the camera position. By optical detection of the spatial marker on the trocar, the camera is then able to determine directly the relative position between the trocar and the camera and thence the instrument arm.

Likewise, with multi-arm robots, when an endoscope is used on an instrument arm there is no longer any need to determine additionally the positions of the other arms: here the positions of the instrument arms are constantly known anyway in each case since the geometry of the whole system is by its nature calibrated or spatially mapped.

As stated in the aforementioned, in a preferred embodiment of the method, a combination arm for a single-port system is used as an instrument arm. In particular, if the endoscope of the single-port robot is used as a camera, only one single position determination is required and this already reflects the relative position with respect to the trocar. The geometries of the remaining instruments with respect to the endoscope are known anyway from the geometry of their permanent fixed arrangement on the instrument arm.

In a preferred embodiment of the method, a visual servoing method is carried out as an error minimization method. In particular, in connection with the use of the endoscope as a mapping camera, visual servoing formulations are particularly suitable for achieving an alignment between the instrument arm and the trocar. The position of the markers or of image features in the current camera image is known. In this way, two different visual servoing formulations may be carried out:

A first formulation is position-based visual servoing. From the projections of the markers in the camera image, that is, from the position of the image features, when there is a known geometry between the markers, for example on the trocar and on the calibrated camera, the position (that is, the position and orientation) of the trocar with respect to the camera's system of coordinates is estimated or determined. Using a suitable control rule as an error minimization method, the endoscope or instrument or an instrument arm can be directed into the previously determined relative position.

Image-based visual servoing provides a second formulation: the projections of the spatial marker in the camera image obtained as in the aforementioned are in this case directed into the desired fixed image positions using a suitable control rule as an error minimization method. Here, therefore, by specifying the relative position, fixed positions of the images of the spatial marker can be established in the camera image.

For image-based visual servoing in particular, if the camera is attached to the instrument arm that is to be adjusted, the following ensues: as soon as the spatial markers are in the desired image position in the camera image, the instrument arm too is automatically located in the desired position, since the camera is arranged in a fixed and known permanent position on the instrument arm and is moved together with said instrument arm.

In principle, both visual servoing formulations or methods can be used in the present case, both methods having advantages and disadvantages. In image-based visual servoing the advantages are predominant here, however, which is why this is the preferred method.

In a preferred embodiment of the method, an image-based visual servoing method is therefore carried out.

In such a method and where there is a camera attached in a fixed manner to the instrument arm, it is necessary, in order to move the camera such that the desired pixels move in a predetermined reference position, to create the mapping rule between a desired pixel alteration, that is, the alteration in the marker image and the corresponding camera position alteration.

In a preferred embodiment, the desired position alteration is determined using an image Jacobian matrix as a mapping rule. The image Jacobian matrix is known, for example, from A. C. Sanderson, L. E. Weiss and C. P. Neuman, 'Dynamic sensor-based control of robots with visual feedback', *IEEE Journal of Robotics and Automation* 3(5) (1987), 404-417 and is used according to the invention in the error minimization method. The control characteristics thereof can then be influenced very effectively using a proportional-integral control rule.

The aforementioned relative position can be set in each case, for example, in the form of 3D-coordinates and angular positions in a spatially fixed 3D-coordinate system in the operating theater.

In a preferred embodiment of the method, however, the relative position is obtained by means of a learning process or what is known as a teach-in step. For example, this involves an instrument arm with an endoscope-camera attached in a fixed manner being moved manually on one occasion into a desired relative position with respect to a trocar and a target image of the trocar marker being recorded using the endoscope. Here the relative position automatically provides the absolute target position. Thus a desired position of the marker points in the camera image appears in the target image, which desired position can then be resumed later. The target position of the marker points in the image is then provided by the teach-in step explained in the aforementioned.

A visual servoing method is known, for example, from J. Wang and W. J. Wilson, '3D relative position and orientation estimation using Kalman filter for robot control', 1992 *IEEE Int. Conf. On Robotics and Automation*, pp. 2638-2645 (1992).

BRIEF DESCRIPTION OF THE DRAWINGS

The invention will now be described in further detail with reference to the exemplary embodiments shown in the drawings. The figures show, in each case illustrated using a drawing in diagram form.

DETAILED DESCRIPTION OF THE INVENTION

Figure 1:
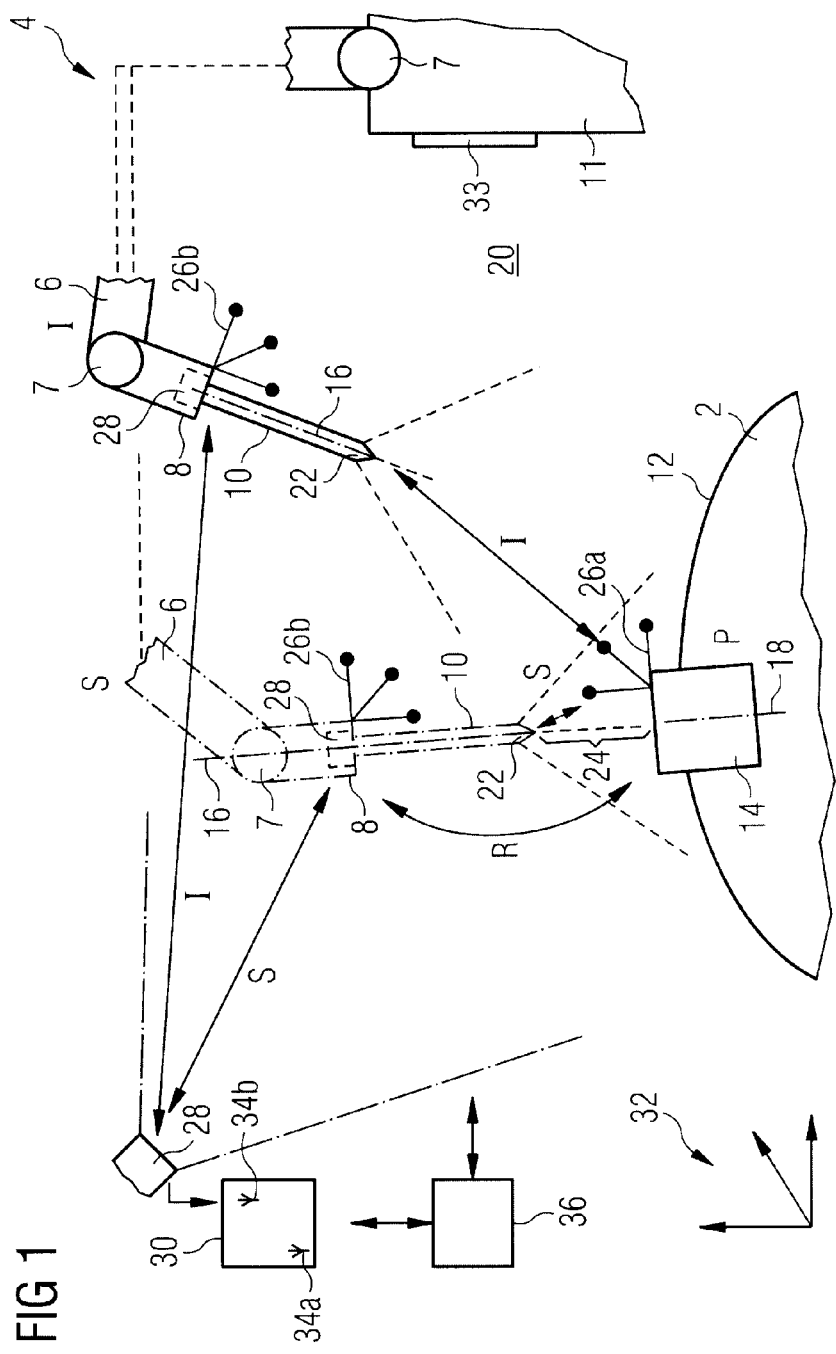
FIG. 1: a patient with an endoscopy robot.

FIG. 1 shows a patient 2, on whom a laparoscopic intervention is to be carried out. On the patient 2 there is therefore a laparoscopy robot 4, comprising an instrument arm 6 that is moveable through a plurality of articulations 7. At its extremity 8, the instrument arm 6 holds an instrument 10 in the form of surgical tongs, with which the intervention is to be carried out.

In order to achieve access to the patient 2, a trocar 14 is inserted into the patient 2, or into an aperture in the patient's abdominal wall 12. In order to gain access into the patient 2, the instrument 10 must be aligned with its central longitudinal axis, that is the instrument axis 16, coaxially to the central longitudinal axis of the trocar 14, and thence to the trocar axis 18, that is, to the central aperture thereof, which is not shown. This and likewise the stylized connection of the instrument arm 6 to a base support 11 on the robot 4 are shown in FIG. 1 with a dotted line.

The alignment is intended to take place outside the patient 2, that is, in the outer area 20, the tip 22 of the instrument 10 still being intended to be at a predetermined distance 24 from the trocar 14. FIG. 1 shows the corresponding position of the instrument arm 6 as the desired position S and simultaneously as the real actual position I, in which it is currently located. According to the inventive method, the instrument arm 6 is intended to be moved from the actual position I into the desired position S.

For this purpose, a spatial marker 26a is applied on the trocar 14. The spatial marker 26a is tracked by a camera 28. The camera 28 shows the spatial marker 26a in a camera image 30. Based on the evaluation of the camera image 30, or of the image of the spatial marker 26a and of the known imaging geometry of the camera 28 and of the position of the camera 28, in for example, a coordinate system 32 that is fixed within the treatment room, the spatial position P of the trocar 14 in the room, and hence in the coordinate system 32 is determined.

In the subsequent step, the actual position I of the instrument arm 6 is determined, for which purpose a spatial marker 26b is likewise applied on an instrument arm 6, which marker is likewise detected and evaluated by the camera 28. The drawing shows the respective images 34a, b of the spatial markers 26a, b in the camera image 30.

The desired position S for the instrument arm 6 is now determined from the actual spatial position P of the trocar 14 and likewise a predeterminable relative position R, which the instrument arm 6 is intended to take up with respect to the trocar 14.

Since all the geometric information is now provided in the coordinate system 32, an error minimization method 36, shown in diagram form, determines appropriate movements for the instrument arm 6 or for the articulations thereof 7 on the basis of the camera image 30 or of the actual position I and of the desired position S. That is, it determines how these movements are to be adjusted in order to move the instrument arm 6 into the desired position S and thus move it into the desired relative position R with respect to the trocar 14.

In a first embodiment, it is indicated, on, for example, a display 33 or in another appropriate manner to an operator, not shown in the drawing, how to adjust each degree of freedom of the instrument arm, for example, the articulations 7, in order to get into the desired position S.

In an alternative embodiment, the articulations 7 are adjusted automatically or mechanically by the robot 4 using the error minimization method 36.

In an alternative embodiment, the trocar 14 is a single-port-trocar. The instrument 10 then consists of a series of individual instruments, arranged in parallel, and not shown, one of which is also generally an endoscope, such that in the method described hereafter, said endoscope may be used to achieve the desired position S, since all the partial instruments, which are in a fixed and known arrangement relative to one another, can also be considered to be a combination instrument 10.

In an alternative embodiment, the instrument 10 is an endoscope, shown by a camera 28, drawn with a dotted line in the instrument arm 6. The respective image area or optical angle of the camera 28 extends from the tip 22 of the instrument 10 (shown with a dotted line). The spatial markers 26b are not present in this case, the camera 28 aligns only the spatial marker 26 on the trocar 14. Since, in this embodiment, the camera inevitably tracks every movement of the instrument arm 6, the camera image 30 and the geometric information obtained therefrom are invariably combined with the real actual position I of the instrument arm 6. The desired position S then corresponds to the relative position R.

Here the error minimization method 36 is carried out in such a way that, in the camera image 30, only the image 34a of the spatial marker 26a can be moved into a consistently predeterminable desired position. This desired position of the image 34a then automatically provides both the desired position S and the desired relative position R or is identical thereto. In this case, the error minimization method 36 is an image-based visual servoing method.

Figure 2:
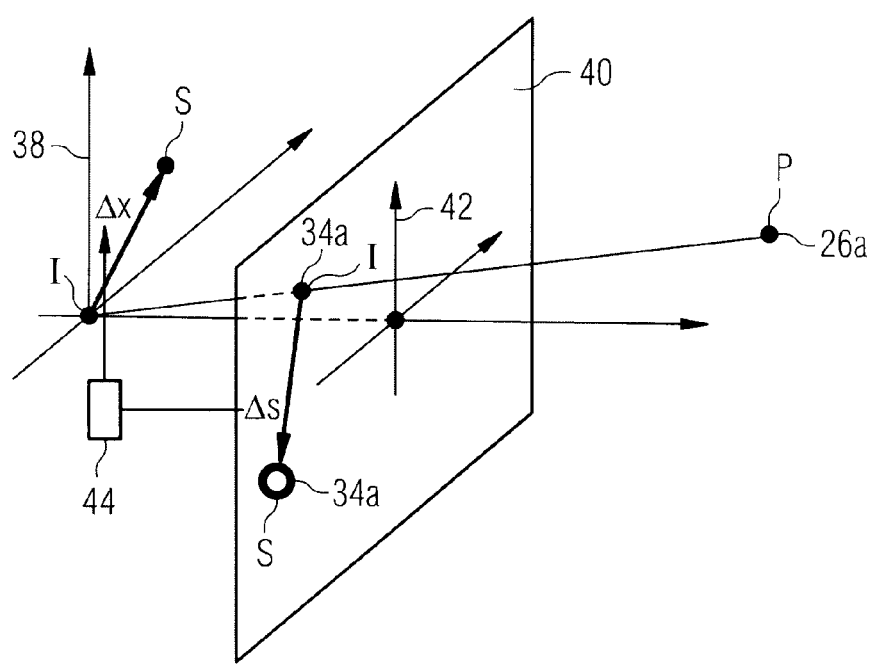
FIG. 2: a visual servoing method with an image Jacobian matrix.

To explain the image-based visual servoing method for the aforementioned endoscopic variant of the method, FIG. 2 shows, instead of the camera 28, the camera coordinate system thereof 38 in the actual position I and, instead of the camera image 30, shows the mapping plane 40 of the camera 28. In addition, the actual spatial position, that is, the spatial position P of the spatial marker 26a is shown symbolically. In the mapping plane 40, the image thereof 34a therefore appears. The mapping plane 40 spans across an image coordinate system 42.

As the result of a preceding teach-in step whereby, in a calibration method, the instrument arm 6 had already been located in the desired position S, that is, in a given relative position R with respect to the spatial marker 26a, the desired position S of the image 34a of the spatial marker 26a is known.

For this purpose, on one occasion only, a camera image 30 has been recorded as a reference image. What now needs to be known is the route that the camera coordinate system 38 (and hence the camera 28) would have to take from the actual position I to the desired position S, so that the image 34a in the mapping plane 40 moves from the actual position I into the desired position S. The calculation is carried out using an image Jacobian matrix 44, which translates the known displacement $\Delta s$ of the image 34a into the actually required displacement $\Delta \chi$ of the camera coordinate system 38 and hence of the camera 28 and hence of the instrument arm 6.

The invention claimed is:

1. A method for moving an instrument arm of a laparoscopy robot into a desired position relative to a trocar placed in a patient, comprising:
    applying a spatial marker on the trocar;
    applying a further spatial marker on the instrument arm;
    arranging a camera on the instrument arm that tracks the spatial marker arranged on the trocar and tracks the further spatial marker arranged on the instrument arm on a camera image;
    detecting a spatial position of the trocar based on the camera image;
    detecting an actual position of the instrument arm based on the camera image; and
    moving the instrument arm from the actual position into the desired position based on the camera image using an error minimization method,
    wherein the desire position is selected to guarantee a coaxial alignment of a central longitudinal axis of an instrument attached to the instrument arm with a central longitudinal axis of the trocar.

2. The method as claimed in claim 1, wherein the instrument arm is moved automatically into the desired position.

3. The method as claimed in claim 1, wherein the instrument arm comprises a combination arm for a single-port system.

4. The method as claimed in claim 1, wherein the error minimization method comprises a visual servoing method.

5. The method as claimed in claim 1, wherein the error minimization method comprises an image-based visual servoing method.

6. The method as claimed in claim 5, wherein the error minimization method is performed using an image Jacobian matrix.

7. The method as claimed in claim 1, wherein the relative position of the instrument arm is determined using a learning method.

* * * * *